United States Patent
Mårtensson et al.

(10) Patent No.: US 10,503,250 B2
(45) Date of Patent: Dec. 10, 2019

(54) SYSTEM AND METHOD FOR SETTING DISPLAY BRIGHTNESS OF DISPLAY OF ELECTRONIC DEVICE

(71) Applicants: Linus Mårtensson, Lund (SE); Ola Thörn, Lund (SE); David De Léon, Lund (SE); Sony Corporation, Tokyo (JP)

(72) Inventors: Linus Mårtensson, Lund (SE); Ola Thörn, Lund (SE); David De Léon, Lund (SE)

(73) Assignee: SONY CORPORATION, Tokyo (JP)

( * ) Notice: Subject to any disclaimer, the term of this patent is extended or adjusted under 35 U.S.C. 154(b) by 371 days.

(21) Appl. No.: 15/033,333

(22) PCT Filed: Feb. 5, 2014

(86) PCT No.: PCT/IB2014/058807
§ 371 (c)(1),
(2) Date: Apr. 29, 2016

(87) PCT Pub. No.: WO2015/118380
PCT Pub. Date: Aug. 13, 2015

(65) Prior Publication Data
US 2016/0266643 A1    Sep. 15, 2016

(51) Int. Cl.
*G09G 5/00* (2006.01)
*G06F 3/01* (2006.01)
(Continued)

(52) U.S. Cl.
CPC .......... *G06F 3/013* (2013.01); *G06K 9/0061* (2013.01); *G09G 3/3208* (2013.01)

(58) Field of Classification Search
USPC ... 345/156, 102, 207, 419, 690, 8, 174, 175; 382/103; 351/204, 210
See application file for complete search history.

(56) References Cited

U.S. PATENT DOCUMENTS

| 3,533,683 A | 10/1970 | Stark |
| 5,910,816 A * | 6/1999 | Fontenot ............ A61B 5/0059 348/162 |

(Continued)

FOREIGN PATENT DOCUMENTS

| JP | 2002 351443 A | 12/2002 |
| JP | 2002351443 | 12/2002 |

(Continued)

OTHER PUBLICATIONS

International Search Report and Written Opinion dated May 27, 2014 for corresponding application No. PCT/IB2014/058807.

(Continued)

*Primary Examiner* — Thuy N Pardo
(74) *Attorney, Agent, or Firm* — Renner, Otto, Boisselle, Sklar

(57) ABSTRACT

The present disclosure provides a system and method of setting a display brightness of a display of an electronic device. One or more images of a user of the electronic device may be captured with a camera of the electronic device. A characteristic of an eye of the user may be detected in the one or more images. A light adaptation state of the user's eye may be determined based on the detected characteristic. The display brightness of the display of the electronic device may be set in view of the determined light adaptation state.

16 Claims, 5 Drawing Sheets

(51) Int. Cl.
*G06K 9/00* (2006.01)
*G09G 3/3208* (2016.01)

(56) References Cited

U.S. PATENT DOCUMENTS

| | | | |
|---|---|---|---|
| 6,090,051 A | 7/2000 | Marshall | |
| 7,367,673 B2* | 5/2008 | McGrath | A61B 3/0091 351/205 |
| 7,742,216 B2 | 6/2010 | Uhlhorn | |
| 7,744,216 B1* | 6/2010 | Uhlhorn | G09G 5/00 351/204 |
| 9,030,532 B2* | 5/2015 | Starkweather | H04N 13/371 348/51 |
| 10,248,842 B1* | 4/2019 | Bardagjy | G06K 9/2027 345/156 |
| 2006/0038880 A1* | 2/2006 | Starkweather | H04N 13/371 348/51 |
| 2006/0114414 A1* | 6/2006 | McGrath | A61B 3/0091 351/246 |
| 2007/0097065 A1* | 5/2007 | Kreek | G06F 1/1626 345/102 |
| 2011/0181541 A1* | 7/2011 | Kuo | G06F 1/1637 345/174 |
| 2012/0288139 A1* | 11/2012 | Singhar | G06F 1/3265 382/103 |
| 2013/0038610 A1* | 2/2013 | Origuchi | G09G 3/003 345/419 |
| 2013/0082991 A1* | 4/2013 | Lin | G09G 5/00 345/207 |
| 2013/0114043 A1* | 5/2013 | Balan | G02B 27/017 351/210 |
| 2013/0135181 A1* | 5/2013 | Eberl | A61B 3/113 345/8 |
| 2013/0222234 A1* | 8/2013 | Tanaka | G09G 5/10 345/156 |
| 2013/0300653 A1* | 11/2013 | Lewis | A61B 3/113 345/156 |
| 2014/0253605 A1* | 9/2014 | Border | G02B 27/0172 345/690 |
| 2014/0375541 A1* | 12/2014 | Nister | G06F 3/013 345/156 |
| 2015/0009121 A1* | 1/2015 | Chuang | G09G 5/10 345/156 |
| 2015/0187330 A1* | 7/2015 | Yang | G09G 5/10 345/690 |
| 2015/0277551 A1* | 10/2015 | Travis | G06F 3/013 345/156 |
| 2016/0018654 A1* | 1/2016 | Haddick | G06T 19/006 345/8 |

FOREIGN PATENT DOCUMENTS

| | | |
|---|---|---|
| WO | 02/064031 A2 | 8/2002 |
| WO | 02064031 | 8/2002 |

OTHER PUBLICATIONS

International Preliminary Report on Patentability dated Aug. 18, 2016 for corresponding application No. PCT/IB2014/058807.

* cited by examiner

SYSTEM AND METHOD FOR SETTING DISPLAY BRIGHTNESS OF DISPLAY OF ELECTRONIC DEVICE

This application is a national phase of International Application No. PCT/IB2014/058807 filed Feb. 5, 2014, the disclosure of which is incorporated herein in its entirety.

TECHNICAL FIELD OF THE INVENTION

The technology of the present disclosure relates generally to setting the display brightness of a display of an electronic device, and more particularly, to a system and method for setting the display brightness of a display of an electronic device based on a light adaptation state of a user's eye.

BACKGROUND

Mobile wireless electronic devices are becoming increasingly popular. For example, mobile telephones, tablets, laptop computers, and portable gaming devices are now in wide-spread use. Many of these devices include a lighted display (e.g., an LED backlit display, an OLED display, etc.). In order to improve the user's ease and/or comfort of viewing the display, the brightness of the display may be adjusted depending on the amount of ambient light in the environment in which the device is used. For example, the ease of reading text displayed on the display in a brightly lit room (a high light intensity environment) may be improved by using a brighter display setting (e.g., to prevent washout). By contrast, it may be preferred to read the same text displayed on the display in a dark room (a low light intensity environment) using a dimmer display setting.

However, control over the brightness of the display continues to be an issue. For example, manual adjustment of the display brightness by the user proves to be inconvenient and cumbersome. In another example, control of the display brightness by automatically adjusting the brightness of the display in accordance with a detection result of a light sensor does not take into consideration the current state of light adaptation of a user's eyes. For example, a display screen that is automatically set to a low brightness level in a low light intensity environment may appear excessively dim to a user that has recently moved from a high light intensity environment to the low light intensity environment. The light sensor cannot be used to accurately determine the amount of time a user has spent in a low light intensity environment and/or a high light intensity environment, as the electronic device is often kept in a pocket or bag. Even in those situations where the electronic device is kept out in the open, the light sensor may be facing a surface (e.g., a table surface) that results in a false reading of the level of ambient light. Furthermore, the light sensor is incapable of knowing if the user has been in a different location than the device.

SUMMARY

The present disclosure describes a device and method for setting the display brightness of an electronic device based on the current state of light adaptation of the user's eye. In accordance with the present disclosure, a characteristic such as the user's pupil size or dilation, and/or the reaction of the user's pupil to display luminance, may be used to determine the light adaptation state of the user's eye and to set the display brightness accordingly. For example, the device and method of the present disclosure may determine whether the user has recently moved from a high light intensity environment to a low light intensity environment (e.g., the user's eye detected as being in an unadapted state), or whether the user has spent a considerable amount of time adjusting to the low light intensity environment (e.g., the user's eye detected as being in an adapted state). Accordingly, the display brightness may be set at least in part based on the light adaptation state of the user, and therefore may avoid a situation where setting the display brightness based on the ambient light would otherwise dictate an unpreferred brightness setting.

According to one aspect of the disclosure, a method of setting a display brightness of a display of an electronic device includes: capturing one or more images of a user of the electronic device with a camera of the electronic device; detecting a characteristic of an eye of the user in the one or more images; determining a light adaptation state of the user's eye based on the detected characteristic; and setting the display brightness of the display of the electronic device based on the determined light adaptation state.

The method may further include illuminating the display during the capturing of the one or more images of the user of the electronic device with the camera. In some embodiments, the illumination of the display includes illuminating the display at a predetermined brightness suitable for use in a high light intensity environment. In other embodiments, illumination of the display includes initially illuminating the display at a low brightness level and increasing the brightness of the display to a predetermined brightness suitable for use in a high light intensity environment. A plurality of images may be captured with the camera and the detected characteristic may be a change in size or dilation of a pupil of the user's eye. In other embodiments, the illumination of the display includes illuminating the display and displaying monochrome red light. The detected characteristic may a size or dilation of a pupil of the user's eye.

In some embodiments, a plurality of images is captured with the camera of the electronic device and the detected characteristic is a change in size or dilation of a pupil of the user's eye. In other embodiments, the detected characteristic is a size or dilation of a pupil of the user's eye. For each image, the size or dilation of the pupil may be determined by calculating a ratio of the diameter of the pupil to the diameter of the iris. The light adaptation state of the user's eye may be determined by comparing the detected characteristic to one or more reference values, each reference value corresponding to a state of light adaptation In some embodiments, the camera is an infrared camera and one or more infrared images are captured of the user of the electronic device.

In some embodiments, the method further includes: determining that the electronic device is presently located in a low light intensity environment; and in response to the determination that that the electronic device is presently located in the low light intensity environment, performing the capturing of the one or more images of the user with the camera, the detecting of the characteristic of the eye of the user in the one or more images, the determining of the light adaptation state of the user's eye based on the detected characteristic, and the setting of the display brightness of the display in view of the determined light adaptation state.

According to another aspect of the disclosure, an electronic device includes a camera, a display, and control circuitry that executes a display brightness function. The display brightness function is configured to control a brightness of the display by: controlling the camera to capture one or more images of a user of the electronic device; detecting a characteristic of an eye of the user in the one or more images; determining a light adaptation state of the user's eye based on the detected characteristic; and setting the display brightness of the display in view of the determined light adaptation state.

The display brightness function may be further configured to control the display to illuminate during the capturing of the one or more images of the user of the electronic device with the camera. In some embodiments, the illumination of the display includes illuminating the display at a predetermined brightness suitable for use in a high light intensity environment. In other embodiments, the illumination of the display includes initially illuminating the display at a low brightness level and increasing the brightness of the display to a predetermined brightness suitable for use in a high light intensity environment. The display brightness function may be configured to capture a plurality of images with the camera, and the detected characteristic may be a change in size or dilation of a pupil of the user's eye. In other embodiments, the illumination of the display includes illuminating the display and displaying monochrome red light. The detected characteristic may be a size or dilation of a pupil of the user's eye.

In some embodiments, the display brightness function is configured to capture a plurality of images with the camera, and the detected characteristic is a change in size or dilation of a pupil of the user's eye. In other embodiments, the detected characteristic is a size or dilation of a pupil of the user's eye. For each image, the display brightness function may be configured to determine the size of the pupil by calculating a ratio of the diameter of the pupil to the diameter of the iris. The light adaptation state of the user's eye may be determined by comparing the detected characteristic to one or more reference values, each reference value corresponding to a state of light adaptation.

In some embodiments, the camera is an infrared camera and one or more infrared images are captured of the user of the electronic device.

In some embodiments, the display brightness function is further configured to: determine that the electronic device is presently located in a low light intensity environment; and in response to the determination that that the electronic device is presently located in the low light intensity environment, perform the controlling of the camera to capture the one or more images of the user of the electronic device, the detecting of the characteristic of the eye of the user in the one or more images, the determining of the light adaptation state of the user's eye based on the detected characteristic, and the setting of the display brightness of the display in view of the determined light adaptation state.

These and further features will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the scope of the claims appended hereto.

DETAILED DESCRIPTION OF EMBODIMENTS

Figure 1:
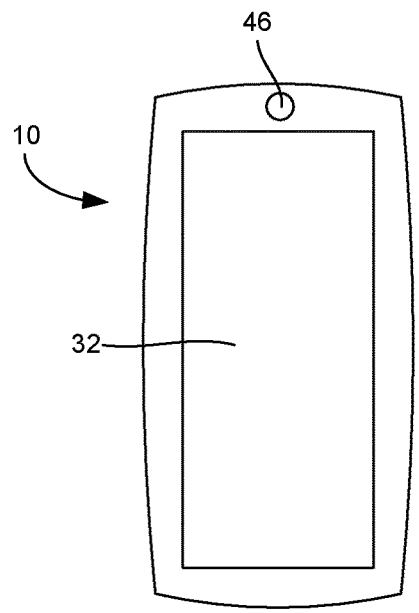
FIG. 1 is a schematic view of a mobile telephone as an exemplary electronic device that includes a brightness setting function in accordance with the present disclosure.

In the description that follows, like components have been given the same reference numerals, regardless of whether they are shown in different embodiments. To illustrate an embodiment(s) of the present invention in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Figure 2:
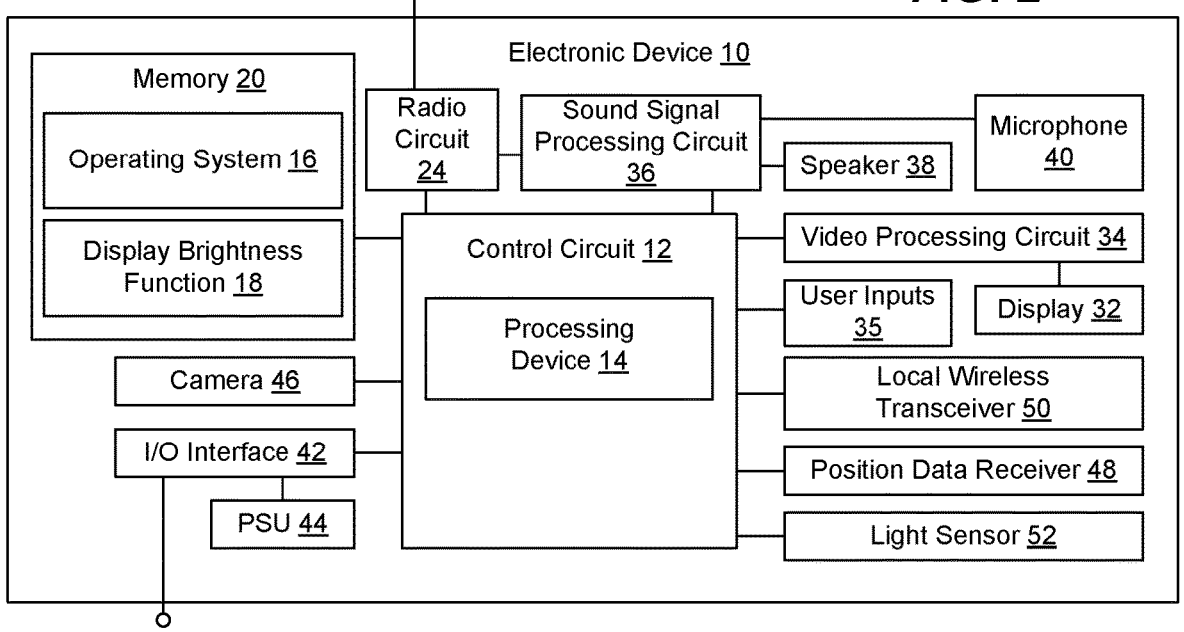
FIG. 2 is a schematic block diagram of the exemplary electronic device of FIG. 1.

Referring initially to FIGS. 1 and 2, an electronic device is shown at 10. The electronic device of the illustrated embodiment is a mobile telephone and will be referred to as the electronic device 10. It will be appreciated that, while embodiments described herein are described primarily in the context of a portable radio communications device such as the illustrated mobile telephone, the exemplary context of a mobile telephone is not the only operational environment in which aspects of the disclosed systems and methods may be used. The techniques described in this document may be applied to any type of appropriate electronic device, examples of which include a mobile telephone, a tablet computing device, a media player, a gaming device, a laptop or desktop computer, an electronic organizer, a personal digital assistant (PDA), a television, a display screen integrated in a vehicle, etc.

The electronic device 10 may include a control circuit 12 that is configured to carry out overall control of the functions and operations of the electronic device 10. The control circuit 12 may include a processing device 14, such as a central processing unit (CPU), microcontroller, or microprocessor. The processing device 14 executes code stored in a memory (not shown) within the control circuit 12 and/or in a separate memory, such as the memory 20, in order to carry out operation of the electronic device 10. For example, the processing device 14 may execute an operating system 16, the display brightness function 18, and/or other applications. In the example shown, the operating system 16 and the display brightness function 18 are stored on the memory 20. In other examples (not shown), the operating system 16 and/or the display brightness function 18 may be stored in a memory within the control circuit 12.

The operating system 16 and/or the display brightness function 18 may be embodied in the form of executable logic routines (e.g., lines of code, software programs, etc.) that are stored on a non-transitory computer readable medium (e.g., the memory 20) of the electronic device 10 and are executed by the control circuit 12 (e.g., using the processing device 14). Furthermore, display brightness function 18 may be a stand-alone software application or form a part of a software application (e.g., a part of the operating system 16) that carries out additional tasks related to the electronic device 10. Also, through the following description, exemplary techniques for setting a display brightness of an electronic device 10 are described. It will be appreciated that through the description of the exemplary techniques, a description of operations that may be carried out in part by executing software is described. The described operations may be considered a method that the corresponding device is configured to carry out. Also, while the display brightness function 18 is implemented in software in accordance with an embodiment, such functionality could also be carried out via dedicated hardware or firmware, or some combination of hardware, firmware and/or software.

The operating system 16 may be executed by the processor processing device 14 to control the allocation and usage of resources in the electronic device 10, as well as provide basic user interface features. Specifically, the operating system 16 may control the allocation and usage of the memory 20, the processing time of the processing device 14 dedicated to various applications being executed by the processing device 14, as well as performing other functionality. In this manner, the operating system 16 may serve as the foundation on which applications, such as the display brightness function 18, depend as is generally known by those with ordinary skill in the art. The operating system 16 also may control much of the user interface environment presented to a user, such as features of the overall graphical user interface (GUI) for the electronic device.

The display brightness function 18 may be configured to control a camera of the electronic device to capture one or more images of a user of the electronic device, detect a characteristic of an eye of the user in the one or more images, determine a light adaptation state of the user's eye based on the detected characteristic, and set the display brightness of the display of the electronic device in view of the determined light adaptation state. In some embodiments, the display brightness function 18 may further be configured to control the display to illuminate during the capturing of the one or more images of the user of the electronic device with the camera. While the display brightness function 18 is described herein as performing each of the above operations, it will be appreciated that the display brightness function 18 may include one or more modules, each module configured to perform one or more dedicated functions. For example, while not specifically shown, the display brightness function 18 may include an image capturing function configured to control a camera of the electronic device to capture one or more images of a user of the electronic device; an image detection function configured to detect a characteristic of an eye of the user in the one or more images; an image analysis function configured to determine a light adaptation state of the user's eye based on the detected characteristic; a display setting function configured to set the display brightness of the display of the electronic device in view of the determined light adaptation state; and/or a display illumination function configured to control the display to illuminate during the capturing of the one or more images of the user of the electronic device with the camera. Additional details and operation of the display brightness function 18 will be described in greater detail below.

The memory 20 may be, for example, one or more of a buffer, a flash memory, a hard drive, a removable media, a volatile memory, a non-volatile memory, a random access memory (RAM), or other suitable device. In a typical arrangement, the memory 20 may include a non-volatile memory for long term data storage and a volatile memory that functions as system memory for the control circuit 12. The memory 20 may exchange data with the control circuit 12 over a data bus. Accompanying control lines and an address bus between the memory 20 and the control circuit 12 also may be present. The memory 20 is considered a non-transitory computer readable medium.

The electronic device 10 includes communications circuitry that enables the electronic device 10 to establish communications with another device. Communications may include calls, data transfers, and the like. Calls may take any suitable form such as, but not limited to, voice calls and video calls. The calls may be carried out over a cellular circuit-switched network or may be in the form of a voice over Internet Protocol (VoIP) call that is established over a packet-switched capability of a cellular network or over an alternative packet-switched network (e.g., a network compatible with IEEE 802.11, which is commonly referred to as WiFi, or a network compatible with IEEE 802.16, which is commonly referred to as WiMAX), for example. Data transfers may include, but are not limited to, receiving streaming content (e.g., streaming audio, streaming video, etc.), receiving data feeds (e.g., pushed data, podcasts, really simple syndication (RSS) data feeds), downloading and/or uploading data (e.g., image files, video files, audio files, ring tones, Internet content, etc.), receiving or sending messages (e.g., text messages, instant messages, electronic mail messages, multimedia messages), and so forth. This data may be processed by the electronic device 10, including storing the data in the memory 20, executing applications to allow user interaction with the data, displaying video and/or image content associated with the data, outputting audio sounds associated with the data, and so forth.

In the exemplary embodiment, the communications circuitry may include an antenna 22 coupled to a radio circuit 24. The radio circuit 24 includes a radio frequency transmitter and receiver for transmitting and receiving signals via the antenna 22.

Figure 3:
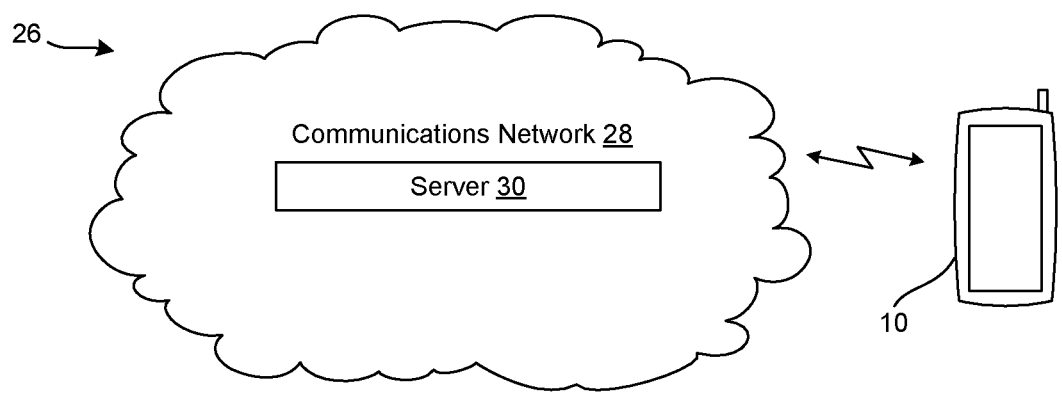
FIG. 3 is a schematic view of a communication system in which the exemplary electronic device of FIG. 1 may operate.

With additional reference to FIG. 3, the radio circuit 24 may be configured to operate in a mobile communications system 26. Radio circuit 24 types for interaction with a mobile radio network and/or broadcasting network include, but are not limited to, global system for mobile communications (GSM), code division multiple access (CDMA), wideband CDMA (WCDMA), general packet radio service (GPRS), long term evolution (LTE), WiFi, WiMAX, digital video broadcasting-handheld (DVB-H), integrated services digital broadcasting (ISDB), high speed packet access (HSPA), etc., as well as advanced versions of these standards or any other appropriate standard. It will be appreciated that the electronic device 10 may be capable of communicating using more than one standard. Therefore, the antenna 22 and the radio circuit 24 may represent one or more than one radio transceiver.

The communications system 26 may include a communications network 28 having a server 30 (or servers) for managing calls placed by and destined to the electronic device 10, transmitting data to and receiving data from the electronic device 10 and carrying out any other support functions. The server 30 communicates with the electronic device 10 via a transmission medium. The transmission medium may be any appropriate device or assembly, including, for example, a communications base station (e.g., a cellular service tower, or "cell" tower), a wireless access point, a satellite, etc. The communications network 28 may support the communications activity of multiple electronic devices 10 and other types of end user devices. As will be appreciated, the server 30 may be configured as a typical computer system used to carry out server functions and may include a processor configured to execute software containing logical instructions that embody the functions of the server 30 and a memory to store such software.

With continued reference to FIGS. 1 and 2, the electronic device 10 may include a display 32. The display 32 displays information to a user such as operating state, time, telephone numbers, contact information, various menus, etc., that enable the user to utilize the various features of the electronic device 10. The display 32 also may be used to visually display content received by the electronic device 10 and/or retrieved from a memory 20 (FIG. 2) of the electronic device 10. The display 32 may be used to present images, video and other graphics to the user, such as photographs, mobile television content, Internet pages, and video associated with games.

The display may be a lighted display. In some embodiments, the display 32 is a backlit liquid-crystal display (LCD). The LCD may be backlit using one or more suitable light sources (e.g., a light emitting diode (LED), cold cathode fluorescent (CCFL), etc.). In other embodiments, the display 14 is an organic light-emitting diode (OLED) display.

The display 14 may be coupled to the control circuit 12 by a video processing circuit 34 that converts video data to a video signal used to drive the display 32. The video processing circuit 34 may include any appropriate buffers, decoders, video data processors and so forth. The video data may be generated by the control circuit 12, retrieved from a video file that is stored in the memory 20, derived from an incoming video data stream that is received by the radio circuit 24, or obtained by any other suitable method.

The electronic device 10 may include one or more user inputs 35 for receiving user input for controlling operation of the electronic device 10. Exemplary user inputs 35 include, but are not limited to, a touch input that overlays the display 32 for touch screen functionality, one or more buttons, motion sensors (e.g., gyro sensors, accelerometers), and so forth.

The electronic device 10 may further include a sound signal processing circuit 36 for processing audio signals. Coupled to the sound signal processing circuit 36 are a speaker 38 and a microphone 40 that enable a user to listen and speak via the electronic device 10, and hear sounds generated in connection with other functions of the device 10. The sound signal processing circuit 36 is coupled to the control circuit 12 so as to carry out overall operation. Audio data may be passed from the control circuit 12 to the sound signal processing circuit 36 for playback to the user. The sound signal processing circuit 36 may include any appropriate buffers, decoders, encoders, amplifiers and so forth.

The electronic device 10 may further include one or more input/output (I/O) interface(s) 42. The I/O interface(s) 42 may be in the form of typical mobile telephone I/O interfaces and may include one or more electrical connectors. The I/O interfaces 42 may form one or more data ports for connecting the electronic device 10 to another device (e.g., a computer) or an accessory (e.g., a headset) via a cable. Further, operating power may be received over the I/O interface(s) 42 and power to charge a battery of a power supply unit (PSU) 44 within the electronic device 10 may be received over the I/O interface(s) 42. The PSU 44 may supply power to operate the electronic device 10 in the absence of an external power source.

The electronic device 10 may further include a camera 46. The camera 46 may be present for taking digital images (e.g., pictures and/or movies). Image and/or video files corresponding to the images taken by the camera 46 may be stored in the memory 20. The camera 46 shown in FIG. 1 is mounted on the same side of the electronic device 10 as the display 32 and faces the same direction as the display 32. Accordingly, the camera 46 may capture an image of a user viewing the display. The camera 46 may include a light as part of the camera assembly (e.g., for capturing an image of the user in a low light intensity environment). As discussed in more detail below, the images taken by the camera 46 may be used by the display brightness function 18 in connection with setting the display brightness of the display 32 of the electronic device 10. In some embodiments, the electronic device 10 may include more than one camera. For example, although not specifically shown in FIG. 1, an additional camera may be located on the side of the electronic device 10 opposite the display 32 and may face the opposite direction as the display 32. In another example, although not specifically shown in FIG. 1, multiple cameras may be mounted on the same side of the electronic device 10 as the display 32 and may face the same direction as the display 32. In some embodiments, the camera 46 or at least one of the cameras included with the electronic device 10 may be an infrared camera.

The electronic device 10 also may include various other components. A position data receiver 48, such as a global positioning system (GPS) receiver, Galileo satellite system receiver or the like, may be involved in determining the location of the electronic device 10. A local transceiver 50, such as an infrared transceiver and/or an RF transceiver (e.g., a Bluetooth chipset) may be used to establish communication with a nearby device, such as an accessory (e.g., a headset), another mobile radio terminal, a computer or another device. A light sensor 52, such as a photodetector may be used to detect the amount of ambient light present in the environment in which the electronic device 10 is located. Accordingly, the light sensor 52 may detect whether the electronic device 10 is presently located in a low light intensity environment or a high light intensity environment.

As used herein, the term "low light intensity environment" is an environment in which the intensity of ambient light is lower than a predetermined intensity. This predetermined intensity may be a value from a standard model, or may be set by the user. Examples of low light intensity environments include an unlit room, a dimly-lit room, a nighttime outdoor setting, etc. Furthermore, the term "high light intensity environment" is an environment in which the intensity of ambient light is equal to or higher than the predetermined intensity. Examples of high light intensity environments include a brightly-lit room, a daytime outdoor setting, etc. The intensity of ambient light in the low light intensity environment is less than the intensity of ambient light in the high light intensity environment.

As described above, the display brightness function 18 of the electronic device 10 may be configured to control a camera of the electronic device to capture one or more images of a user of the electronic device, detect a characteristic of an eye of the user in the one or more images, determine a light adaptation state of the user's eye based on the detected characteristic, and set the display brightness of the display of the electronic device in view of the determined light adaptation state. In some embodiments, the display brightness function 18 may further be configured to control the display to illuminate during the capturing of the one or more images of the user of the electronic device with the camera. The display brightness function 18 may be configured to perform such functionality in response to an instruction to illuminate the display. For example, a user of the display may press a button on the device or touch a portion of the touch input, thereby prompting the electronic device to turn on or "wake-up".

In some embodiments, the display brightness function 18 may be configured to perform the described functionality each time the display is turned on. In other embodiments, the display brightness function 18 may be configured to perform the described functionality only in specific lighting environments. For example, the process performed by the display brightness function may in some implementations only be performed when it is detected that the electronic device 10 is present in a low light intensity environment. Accordingly, the display brightness function 18 may be configured to determine whether the electronic device 10 is located in a low light intensity environment prior to performing the described functionality. Such determination may be made using information received from the light sensor 52.

The display brightness function 18 may control the camera 46 of the electronic device 10 to capture one or more images of the user of the electronic device. In some embodiments, the one or more images may be captured by the camera 46 of the electronic device 10 once the display is illuminated. In other embodiments, (e.g., where the camera used to capture the one or more images of the user may be an infrared camera) the one or more images may be captured by the camera 46 of the electronic device 10 without illumination of the display. In some embodiments where more than one image is captured, as few as two pictures may be taken. In other embodiments where more than one image is captured, several pictures may be taken.

The one or more images may be captured over a given time period, the images being captured at respective intervals within the given time period. The given time period in which the one or more images may be captured may be any suitable time period that allows for a sufficient number of images to be captured for use in detecting a characteristic of an eye of a user. For example, the given time period may be one second or less. In another example, the given time period may range from one to two seconds. In another example, the given time period may range from two to three seconds. The given time period may depend on such factors as the speed of the camera 46, the processing speed of the electronic device 10, etc. The respective intervals between the captured images may also be set in any suitable manner. In one example, the interval is the same between each respective captured image. In another example, the duration of the interval between respective captured images may be shortened during a part of the predetermined period (e.g., during the beginning of the predetermined period).

In some embodiments, the camera 46 may be used to take video of the user during the given time period. In such embodiments, one or more frames of the video may serve as the captured image(s).

The display brightness function 18 may control the display 32 to illuminate during the capturing of the one or more images of the user of the electronic device with the camera 46 (e.g., during the given time period). In some embodiments, the display may be illuminated at a predetermined brightness. This predetermined brightness may be set at a relatively high level (e.g., the brightest setting available, or a brightness setting corresponding to a setting typically more appropriate for a high light intensity environment, which may be the brightest setting available). In other embodiments, the display may initially be illuminated at a relatively low brightness setting, and may be increased to the predetermined brightness. Ramping up the brightness of the display may be preferred to a user as opposed to initially exposing the user to the predetermined brightness. The one or more images can still be captured during the brightness ramp up.

In a low light intensity environment, the light emitted from the display 32 may at least partially illuminate the face of a user so that the camera 46 can capture an image of the user's face. This may enable the camera to capture the image of the user, particularly when other ambient light is insufficient for yielding a discernible image.

In some embodiments, the display 32 may display a screen associated with the user interface of the device (e.g., a lock screen, home screen, open application, etc.) during the illumination. In other embodiments, the display may display a pre-set image and/or color setting (e.g., a white screen, a red screen, a monochrome red image) during the illumination. Use of a pre-set image and/or color setting may reduce the occurrence of erroneous detection (e.g., due to a lock screen or home screen displaying an image that is relatively dark).

In some embodiments, illumination of the display 32 is intended to cause user's pupil to change in size (e.g., contract), and this change in size (or the absence thereof) may be used in subsequent detection and determination performed by the display brightness function 18. In other embodiments, the detection and determination is based on the size (e.g., the absolute size) or dilation of the pupil (as opposed to the change in size or dilation of the pupil), and illumination of the display 32 may be performed so that it does not cause a change in dilation of the eye. For example, red light may be emitted from the display 32 (e.g., as a red screen, as a monochrome red image, etc.). The red light may either initially be emitted at a predetermined brightness or ramped up from a lower brightness to the predetermined brightness. The red light may at least partially illuminate the face of the user, but will not cause the dilation of the eye to change, and will thereby permit the detection of the pupil size or dilation. This approach utilizes the fact that red light does not impede the dark adaptation since the rods (the retinal cells that are responsible for vision in low light) are insensitive to red light. The insensitivity of rods to long-wavelength light has led to the use of red lights under certain special circumstances (e.g., in the control rooms of submarines, in research laboratories, aircraft, or during naked-eye astronomy).

In another example in which an infrared camera 46 is used to capture the one or more images of the user, the display 32 may not be illuminated during such capturing.

While the embodiments described above may utilize luminance from the display 32 during the capturing of the one or more images of the user of the electronic device with the camera 46, in some embodiments the luminance may instead be provided by a light included as part of the camera assembly of the camera 46. In such embodiments, the light may be controlled to emulate the brightness associated with illumination of the display at the predetermined brightness.

The display brightness function 18 may detect a characteristic of an eye of the user in the one or more images. In some embodiments, the detected characteristic is the change in the size or dilation of the user's pupil, which may be detected using two or more images captured by the camera. The detection based on the change in size or dilation may take into consideration the rate at which the size or dilation is changed. In other embodiments, the detected characteristic is the size or dilation of the user's pupil, which may be detected using a single image captured by the camera (or by using more than one image to obtain an average size or dilation of the user's pupil).

For each captured image used to detect the characteristic of the eye of the user, the image may be analyzed to identify the eye (and the pupil) of the user. For example, the eye (pupil) of the user may be identified using a suitable recognition algorithm. Such recognition algorithms are well known in the art and commercially available.

Figure 4A:
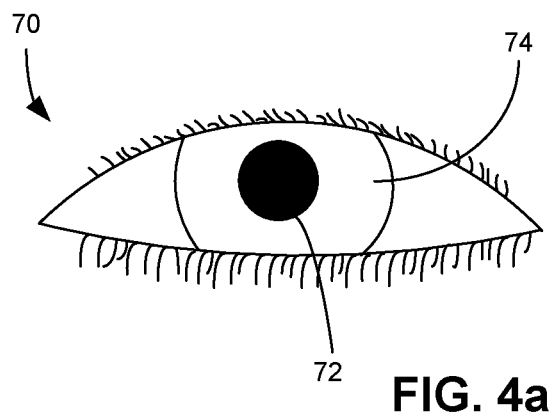
FIGS. 4a-4c are respective schematic views of an eye as imaged by a camera of the exemplary electronic device of FIG. 1.
Figure 4B:
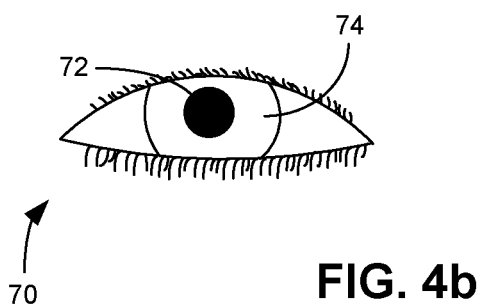
Figure 4C:
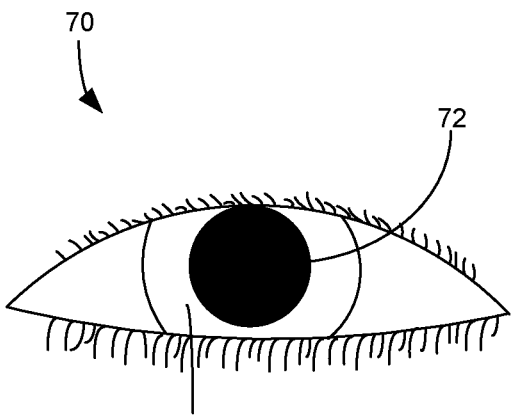

For each captured image, the size and/or dilation of the identified pupil may be measured. In some embodiments, the size of the pupil may be detected as part of the recognition algorithm. In other embodiments, the dilation of the identified pupil may be measured by calculating a ratio of the diameter of the pupil to the diameter of the iris. Reference is made to FIGS. 4a-4c, which schematically shows respective images of an eye 70 that may be subjected to detection. Because the absolute size of the pupil 72 varies with distance to the camera 46 (e.g., as shown in FIGS. 4a and 4b), measurement of the ratio of the diameter of the pupil 72 to the diameter of the iris 74 may be used to provide a detectable metric independent of the distance of the user to the camera. For example, the ratio of the diameter of the pupil 72 to the diameter of the iris 74 of the eye 70 shown in FIG. 4a may be 0.5. Although the overall size of the eye 70 as shown in FIG. 4b is smaller than the eye 70 as shown in FIG. 4a, the ratio of the diameter of the pupil 72 to the diameter of the iris 74 of the eye 70 as shown in FIG. 4b may also be 0.5. And while the overall size of the eye 70 as shown in FIG. 4c is the same as the eye 70 as shown in FIG. 4a, the ratio of the diameter of the pupil 72 to the diameter of the iris 74 of the eye 70 as shown in FIG. 4c may be different (e.g., 0.75). Such calculation may allow for the detection to differentiate a situation where a user moves relative to the camera 46 from a situation where the dilation of the pupil is changed.

The display brightness function 18 may determine the light adaptation state of the user's eye based on the detected characteristic. The detected characteristic may be identified using a detected value (e.g., a size measurement, a ratio value, an amount of change in a size measurement, or an amount of change in a ratio value). Accordingly, in some embodiments, the display brightness function 18 determines the light adaptation state of the user's eye using a detected value that corresponds to the detected amount of change in size and/or dilation of the pupil in response to illuminating the display. In other embodiments, the display brightness function 18 determines the light adaption state of the user's eye using a detected value that corresponds to the size and/or dilation of the pupil.

In some embodiments, the value detected by the display brightness function 18 may be compared to one or more predetermined values. For example, the value detected by the display brightness function 18 may be compared against a value that has previously been calibrated for the user. The memory 20 may store a table of pupil sizes (and/or changes in pupil size) of the user of the device that has been previously gathered using the front camera of the device during different luminance conditions. In another example, the value detected by the display brightness function 18 may be compared against a value from a standard model (e.g., stored in the memory 20).

Based on the comparison, the display brightness function 18 may determine the light adaptation state of the user's eye. For example, where the detected value corresponds to the detected amount of change in size and/or dilation of the pupil in response to illuminating the display, a value larger than the predetermined value may indicate that the user is presently in an adapted state. Similarly, a value smaller than the predetermined value may indicate that the user is presently in an unadapted state. In another example, where the detected value corresponds to the detected size and/or dilation of the pupil, a value larger than the predetermined value may indicate that the user is presently in an adapted state. Similarly, a value smaller than the predetermined value may indicate that the user is presently in an unadapted state.

In some embodiments, the display brightness function 18 may determine a degree of light adaptation. This may be implemented by comparing the detected value to more than one predetermined value.

The display brightness function 18 may set the display brightness of a display of the electronic device in view of the detected characteristic. For example, in an embodiment where the user and electronic device are located in a low light intensity environment, the display may be displayed using a low brightness setting if it is determined that the user is in an adjusted state. If it is determined that the user is not in an adjusted state, the display may be displayed using a high brightness setting. The high brightness setting is brighter than the low brightness setting.

In embodiments where the display brightness function 18 determines the degree of light adaptation, the varying degrees of light adaptation may be associated with different respective brightness settings.

In some embodiments, subsequent to setting the display brightness, the display brightness may be gradually adjusted to a display brightness typically associated with the environment in which the electronic device 10 is located. For example, if the electronic device 10 is located in a low light intensity environment and the display is set to a high brightness based on a determination that the user is not in an adjusted state, the display brightness function may gradually decrease the display brightness to a lower setting over a period of time in order to allow the eyes of the user to adjust to the low light intensity environment. In some examples, this decrease may be performed over a period ranging from one to three minutes. In other examples, this decrease may be performed over a period ranging from three to five minutes.

As described above, the display brightness application takes into consideration the light adaptation state of the user's eye, as opposed to simply relying on the present state of the ambient light. For example, if a user has recently moved from a high light intensity environment to a low light intensity environment, the user's eyes may not be adjusted to the low light intensity environment. The user's pupils will tend to be smaller and will not contract as quickly in response to the light emitted from the display. In this case, the display luminance may be higher so that the display does not appear dim to the user. As another example, if the user has been in a low light intensity environment for a while, the user's eyes may be dark adjusted. The pupils will tend to be larger and will also react more strongly to the light emitted from the display. In this case, the display luminance may be set lower so not to overpower the viewing experience of the user.

Figure 5:
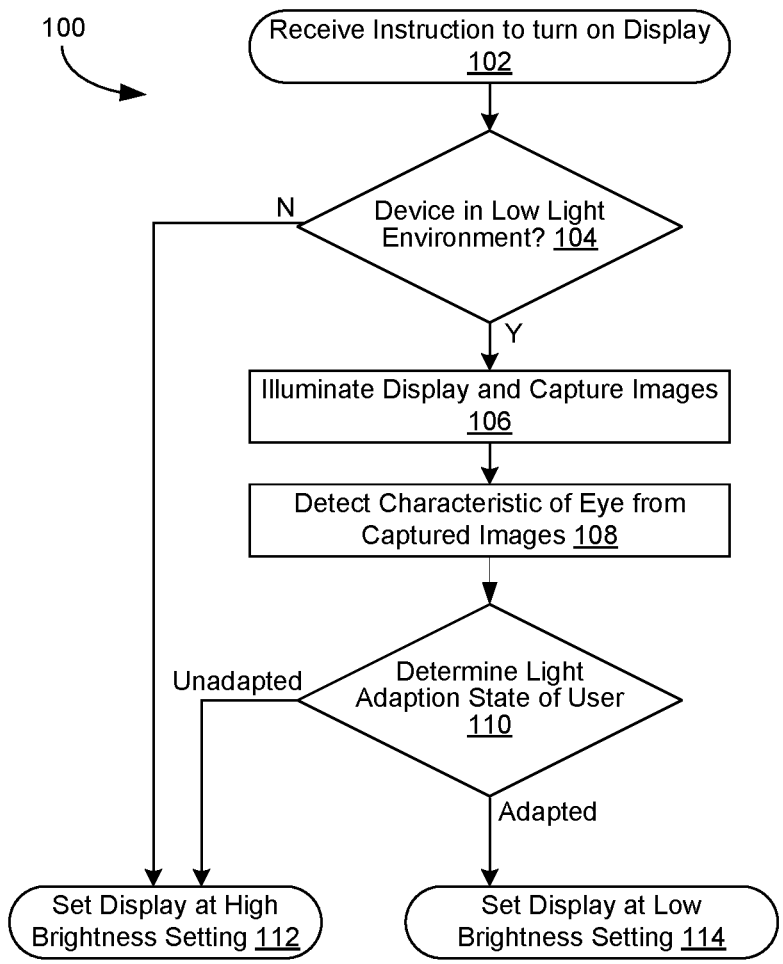
FIGS. 5-7 are flow diagrams representing respective exemplary methods of setting display brightness.
Figure 6:
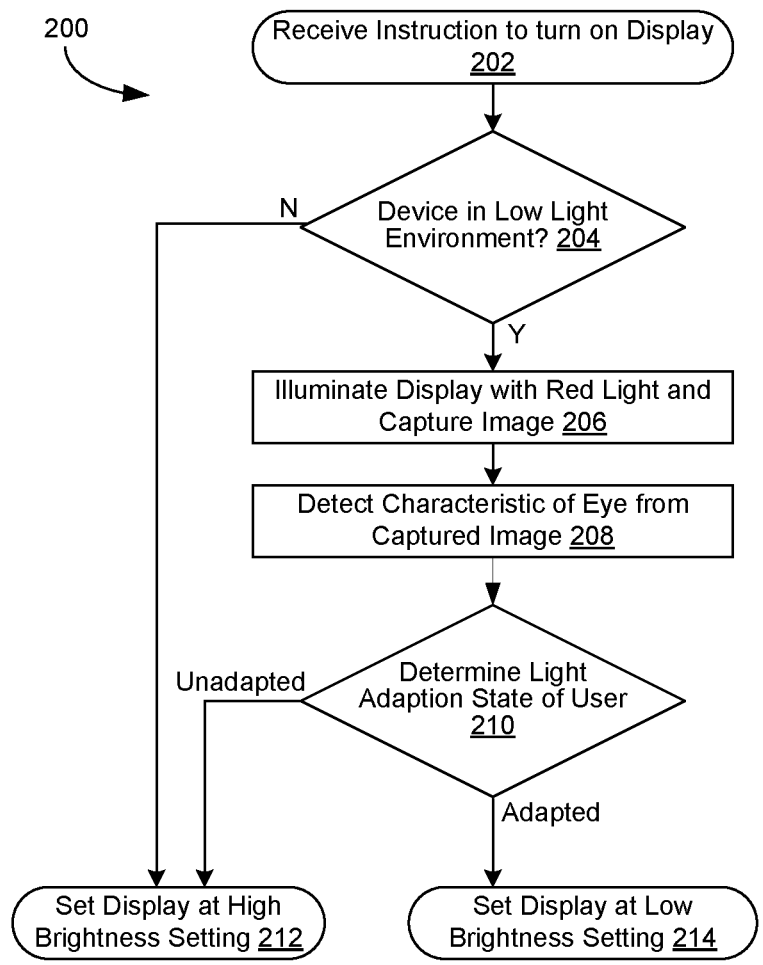
Figure 7:
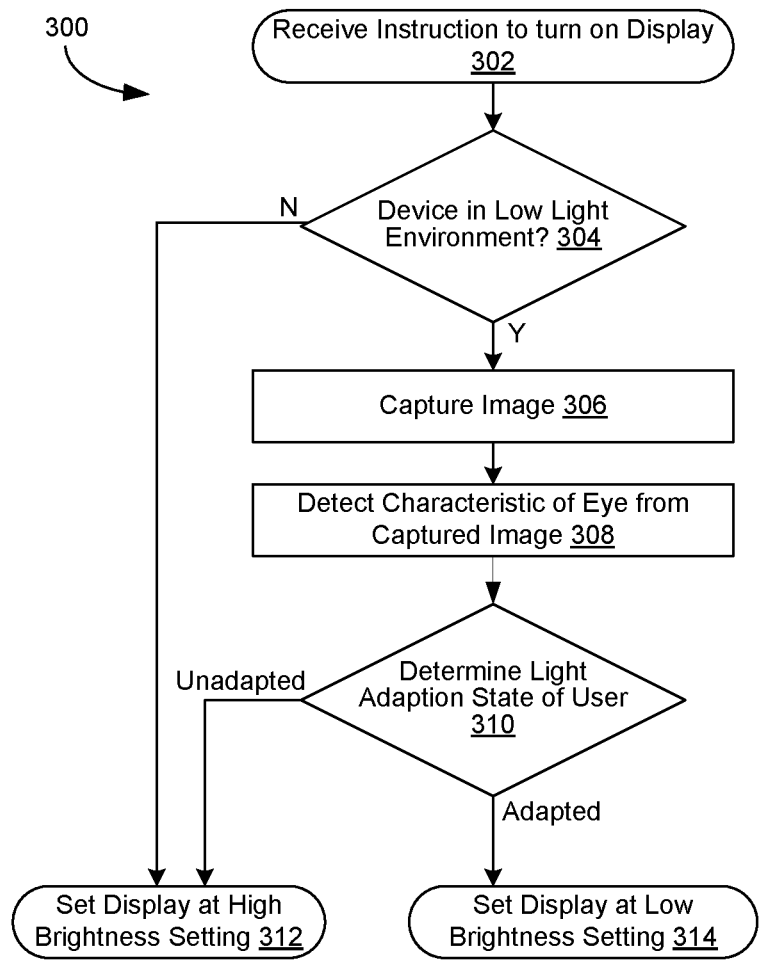

The features of the display brightness function are exemplified in FIGS. 5-7, which show logical operations for implementing respective exemplary methods of setting a display brightness of an electronic device based on a light adaptation state of the user's eye. Each of the exemplary methods may be carried out by executing an embodiment of the display brightness function 18, for example. Although FIGS. 5-7 each show a specific order of logical operations, the order thereof may be changed relative to the order shown. Also, two or more logical operations shown in succession may be executed concurrently or with partial concurrence. Certain logical operations also may be omitted.

FIG. 5 shows logical operations for implementing an exemplary method 100. In the exemplary method shown in FIG. 5, the display brightness function is configured to determine the state of light adaptation of the user's eye based on a change in size or dilation of the pupil in response to illuminating the display. The logical flow may begin at 102 where the electronic device receives an instruction to turn on the display. This instruction may be provided to the display as a result of the user of the electronic device 10 pressing a button (e.g., to "wake up" the electronic device).

At 104, the display brightness function 18 determines whether the device is presently located in a low light intensity environment (e.g., using the light sensor). If it is determined that the device is not presently located in a low light intensity environment (i.e., the device is instead presently located in a high light intensity environment), the display is displayed using a high brightness setting at 112. If it is determined that the device is presently located in a low light intensity environment, the display brightness function 18 may proceed to 106.

At 106, the display brightness function 18 controls the display to illuminate. As described above, in one example, the display may be illuminated at a predetermined brightness (e.g., the brightest setting available, or a brightness setting corresponding to a setting typically more appropriate for a high light intensity environment). In another example, the display may initially be illuminated at a low brightness setting, and may be increased to the predetermined brightness. The display may be illuminated fir a given time period.

Furthermore, at 106, the display brightness function 18 controls the camera to capture images the face of the user during illumination of the display. For example, as the display is illuminated, more than one picture is taken over the given time period.

At 108, the display brightness function detects a characteristic of the eye of the user in the images captured by the camera. Each image may be analyzed to identify the eye (e.g., the pupil) of the user, and the size or dilation of the identified pupil is measured. The size or dilation of the identified pupil in each image is compared to determine the amount of change of the pupil.

At 110, the display brightness function determines the light adaptation state of the user's eye based on the detected change in the size or dilation of the identified pupil. More specifically, at 110, the display brightness function 18 determines whether the size or dilation of the pupil has changed more than a predetermined amount. If it is determined that the size or dilation of the pupil has changed greater than a predetermined amount, it is determined that the eye of the user is adapted to the low light intensity environment and the display is displayed using a low brightness setting at 114. If it is determined that the size or dilation of the pupil has not changed greater than a predetermined amount, it is determined that the eye of the user is not adapted to the low light intensity environment and the display is displayed using a high brightness setting at 112.

FIG. 6 shows logical operations for implementing another exemplary method. In the exemplary method shown in FIG. 6, the display brightness function is configured to determine the state of light adaptation of the user's eye based on the present size or dilation of the pupil, rather than the response of the pupil to illumination. The logical flow may begin at 202 where the electronic device receives an instruction to turn on the display. This instruction may be provided to the display as a result of the user of the electronic device 10 pressing a button (e.g., to "wake up" the electronic device).

At 204, the display brightness function 18 determines whether the device is presently located in a low light intensity environment (e.g., using the light sensor). If it is determined that the device is not presently located in a low light intensity environment (i.e., the device is present located in a high light intensity environment), the display is displayed using a high brightness setting at 212. If it is determined that the device is presently located in a low light intensity environment, the display brightness function 18 may proceed to 206.

At 206, the display brightness function controls the display to illuminate red light. As discussed above, in one example, the display may be illuminated at a predetermined brightness (e.g., the brightest setting available, or a brightness setting corresponding to a setting typically more appropriate for a high light intensity environment). In another example, the display may initially be illuminated at a low brightness setting, and may be increased to the predetermined brightness. The red light may at least partially illuminate the face of the user, but will not cause the dilation of the eye to change.

Furthermore, at 206, the display brightness function controls the camera to capture an image of the face of the user during illumination of the display.

At 208, the display brightness function detects a characteristic of the eye of the user in the images captured by the camera. Specifically, the image may be analyzed to identify the eye (e.g., the pupil) of the user, and the size or dilation of the identified pupil may be measured.

At 210, the display brightness function determines the light adaptation state of the user's eye based on the detected size or dilation of the identified pupil. More specifically, at 210, the display brightness function 18 determines whether the size or dilation of the pupil is greater than a predetermined amount. If it is determined that the size or dilation of the pupil is greater than a predetermined amount, the display is displayed using a low brightness setting at 214. If it is determined that the size or dilation of the pupil lower than a predetermined amount, the display is displayed using a high brightness setting at 212.

FIG. 7 shows logical operations for implementing another exemplary method. In the exemplary method shown in FIG. 7, the display brightness function is configured to determine the state of light adaptation of the user's eye based on the present size or dilation of the pupil, rather than the response of the pupil to illumination. This exemplary method also does not include the use of visible light. The logical flow may begin at 302 where the electronic device receives an instruction to turn on the display. This instruction may be provided to the display as a result of the user of the electronic device 10 pressing a button (e.g., to "wake up" the electronic device).

At 304, the display brightness function 18 determines whether the device is presently located in a low light intensity environment (e.g., using the light sensor). If it is determined that the device is not presently located in a low light intensity environment (i.e., the device is present located in a high light intensity environment), the display is displayed using a high brightness setting at 212. If it is determined that the device is presently located in a low light intensity environment, the display brightness function 18 may proceed to 306.

At 306, the display brightness function causes the infrared camera to capture an image of the user. The infrared camera may image the face of the user and will not cause the dilation of the eye to change.

At 308, the display brightness function detects a characteristic of the eye of the user in the images captured by the camera. Specifically, the image may be analyzed to identify the eye (e.g., the pupil) of the user, and the size or dilation of the identified pupil may be measured.

At 310, the display brightness function determines the light adaptation state of the user's eye based on the detected size or dilation of the identified pupil. More specifically, at 310, the display brightness function 18 determines whether the size or dilation of the pupil is greater than a predetermined amount. If it is determined that the size or dilation of the pupil is greater than a predetermined amount, the display is displayed using a low brightness setting at 314. If it is determined that the size or dilation of the pupil lower than a predetermined amount, the display is displayed using a high brightness setting at 312.

Although certain embodiments have been shown and described, it is understood that equivalents and modifications falling within the scope of the appended claims will occur to others who are skilled in the art upon the reading and understanding of this specification.

What is claimed is:

1. A method of setting a display brightness of a display of an electronic device, comprising:
   capturing one or more images of an eye of a user of the electronic device with a camera of the electronic device;
   illuminating the display during the capturing of the one or more images of the user of the electronic device with the camera, wherein the illumination of the display comprises illuminating the display and displaying monochrome red light;
   analyzing the one or more images of the eye of the user to detect a characteristic of the eye of the user;
   determining a light adaptation state of the user's eye based on the detected characteristic; and
   setting the display brightness of the display of the electronic device based on the determined light adaptation state of the user's eye.

2. The method of claim 1, wherein the illumination of the display comprises illuminating the display at a predetermined brightness suitable for use in a high light intensity environment.

3. The method of claim 2, wherein a plurality of images are captured with the camera and the detected characteristic is a change in size or dilation of a pupil of the user's eye.

4. The method of claim 1, wherein the illumination of the display comprises initially illuminating the display at a low brightness level and increasing the brightness of the display to a predetermined brightness suitable for use in a high light intensity environment.

5. The method of claim 1, wherein a plurality of images are captured with the camera of the electronic device and the detected characteristic is a change in size or dilation of a pupil of the user's eye.

6. The method of claim 1, wherein the detected characteristic is a size or dilation of a pupil of the user's eye.

7. The method of claim 1, wherein the camera is an infrared camera and one or more infrared images are captured of the user of the electronic device.

8. The method of claim 1, further comprising:
   determining that the electronic device is presently located in a low light intensity environment; and
   in response to the determination that that the electronic device is presently located in the low light intensity environment, performing the capturing of the one or more images of the user with the camera, the detecting of the characteristic of the eye of the user in the one or more images, the determining of the light adaptation state of the user's eye based on the detected characteristic, and the setting of the display brightness of the display in view of the determined light adaptation state.

9. An electronic device, comprising:
   a camera;
   a display; and
   control circuitry that executes a display brightness function configured to control a brightness of the display by:
      controlling the camera to capture one or more images of an eye of a user of the electronic device;
      controlling the display to illuminate during the capturing of the one or more images of the user of the electronic device with the camera, wherein the illumination of the display comprises illuminating the display and displaying monochrome red light;
      analyzing the one or more images of the eye of the user to detect a characteristic of the eye of the user;
      determining a light adaptation state of the user's eye based on the detected characteristic; and
      setting the display brightness of the display in view of the determined light adaptation state of the user's eye.

10. The electronic device of claim 9, wherein the illumination of the display comprises illuminating the display at a predetermined brightness suitable for use in a high light intensity environment.

11. The electronic device of claim 10, wherein the display brightness function is configured to capture a plurality of images with the camera, and the detected characteristic is a change in size or dilation of a pupil of the user's eye.

12. The electronic device of claim 9, wherein the illumination of the display comprises initially illuminating the display at a low brightness level and increasing the brightness of the display to a predetermined brightness suitable for use in a high light intensity environment.

13. The electronic device of claim 9, wherein the display brightness function is configured to capture a plurality of images with the camera, and the detected characteristic is a change in size or dilation of a pupil of the user's eye.

14. The electronic device of claim 9, wherein the detected characteristic is a size or dilation of a pupil of the user's eye.

15. The electronic device of claim 9, wherein the camera is an infrared camera and one or more infrared images are captured of the user of the electronic device.

16. The electronic device of claim 9, wherein the display brightness function is further configured to:
   determine that the electronic device is presently located in a low light intensity environment; and
   in response to the determination that that the electronic device is presently located in the low light intensity environment, perform the controlling of the camera to capture the one or more images of the user of the electronic device, the detecting of the characteristic of the eye of the user in the one or more images, the determining of the light adaptation state of the user's eye based on the detected characteristic, and the setting of the display brightness of the display in view of the determined light adaptation state.

* * * * *